(12) United States Patent
Robb et al.

(10) Patent No.: US 6,669,934 B1
(45) Date of Patent: Dec. 30, 2003

(54) METHOD OF MODULATING FERTILITY IN ANIMALS BY IL-11

(75) Inventors: Lorraine Grace Robb, North Melbourne (AU); Harshal Hanumant Nandurkar, Glen Waverley (AU); Colin Glenn Begley, Donvale (AU)

(73) Assignee: Amrad Operations, Pty. Ltd., Richmond (AU)

( * ) Notice: Subject to any disclaimer, the term of this patent is extended or adjusted under 35 U.S.C. 154(b) by 0 days.

(21) Appl. No.: 09/331,569

(22) PCT Filed: Dec. 24, 1997

(86) PCT No.: PCT/AU97/00880

§ 371 (c)(1),
(2), (4) Date: Aug. 27, 1999

(87) PCT Pub. No.: WO98/27996

PCT Pub. Date: Jul. 2, 1998

(30) Foreign Application Priority Data

Dec. 24, 1996 (AU) .............................................. PO4393

(51) Int. Cl.[7] ........................ A61K 45/00; A61K 38/00; C07K 17/00
(52) U.S. Cl. ........................ 424/85.2; 424/85.1; 514/2; 514/12; 530/351
(58) Field of Search ............................... 424/85.1, 85.2; 514/2, 12, 21; 435/440; 530/351

(56) References Cited

U.S. PATENT DOCUMENTS 5,437,863 A   8/1995   Williams et al.

FOREIGN PATENT DOCUMENTS

| JP | 06256399 A | 9/1994 |
|---|---|---|
| WO | WO 91/07495 | 5/1991 |
| WO | WO 94/02502 | 2/1994 |
| WO | WO 94/05318 | 3/1994 |
| WO | WO 95/24650 | 9/1995 |
| WO | WO 96/03143 A1 | 2/1996 |
| WO | WO 96/07737 | 3/1996 |
| WO | WO 96/09382 | 3/1996 |
| WO | WO 96/18648 | 6/1996 |
| WO | WO 96/38570 | 12/1996 |
| WO | WO 96/41607 | 12/1996 |
| WO | WO 97/01353 | 1/1997 |
| WO | WO 97/24373 | 7/1997 |

OTHER PUBLICATIONS

Dimitriadis et al. Expression of interleukin–11 during the human menstrual cycle: coincidence with stromal cell decidualization and relationship to leukaemia inhibitory factor and prolactin. (2000), Molecular Human Reproduction, vol. 6: 907–914.*

Nandurkar, Harshal, et al. (Sep. 5, 1997, Adult Mice With Targeted Mutation of the Interleukin–II REceptor (IL–IIRa) Display Normal Hematopoiesis Blood. vol. 90, No. 6: 2148–2159.

* cited by examiner

*Primary Examiner*—Lorraine Spector
*Assistant Examiner*—Jegatheesan Seharaseyon
(74) *Attorney, Agent, or Firm*—Scully, Scott, Murphy & Presser

(57) ABSTRACT

The present invention relates to a method for modulating fertility in an animal by administering an effective amount of IL-11 or derivatives or homologues thereof or an effective amount of an agonist or antagonist of the interaction between IL-11 and IL-11Rα.

5 Claims, 10 Drawing Sheets

US 6,669,934 B1

METHOD OF MODULATING FERTILITY IN ANIMALS BY IL-11

FIELD OF THE INVENTION

The present invention relates generally to a method for controlling fertility and/or modulating the maintenance of pregnancy in animals. The present invention further provides an animal model useful for screening for therapeutic agents to treat infertility, to prevent or reduce spontaneous abortion and/or as contraceptive agents in animals.

Bibliographic details of the publications numerically referred to in this specification are collected at the end of the description. Sequence Identity Numbers (SEQ ID Nos.) for the nucleotide and amino acid sequences referred to in the specification are defined following the bibliography.

BACKGROUND OF THE INVENTION

The increasing sophistication of recombinant DNA technology is greatly facilitating research and development in the medical and allied health fields. A particularly important area of research involves cytokines and growth factors and their putative roles in fertility, birth control and pregnancy maintenance in humans and animals.

Approximately one third of normal human pregnancies end in spontaneous abortion and about one fifth of these during the very early stages of pregnancy. In the animal and livestock industry, spontaneous abortion is a major economic consideration. There is a need, therefore, to further investigate the basis behind spontaneous abortion and to develop appropriate therapeutic means for reducing its occurrence. There is also a need to investigate ways of improving the fertility rates of animals and to treat infertility in males and females. In work leading up to the present invention, the inventors investigated the role of IL-11 in fertility and pregnancy.

Interleukin(IL)-11 (IL-11) is a cytokine with many biological actions (1). It was originally cloned based on its ability to stimulate proliferation of a murine IL-6 dependent plasmacytoma cell line (2) and to inhibit adipogenesis (3). Within the hematopoietic system, IL-11 actions include stimulation of multipotential progenitors (4) and effects on erythropoiesis (5), megakaryopoiesis (6) and B lymphocyte maturation (7). IL-11 also stimulates acute phase protein synthesis (8), regulates neuronal differentiation (9) and acts in osteoclast development (10). In vivo, IL-11 has been demonstrated to stimulate multilineage hematopoietic reconstitution and enhance recovery of intestinal epithelial cells and spermatogenesis after cytotoxic therapy (11, 12, 13).

Many of the activities of IL-11 are shared with other cytokines including IL-6, leukemia inhibitory factor (LEF), ciliary neurotrophic growth factor (CNTF) and oncostatin M (OSM) (12, 14, 15, 16, 17). These cytokines elicit their actions by binding to multi-subunit receptor complexes expressed on the surface of target cells and their overlapping biological functions may, in part, be attributable to the sharing of receptor subunits. The receptors involved in the formation of these complexes are members of the hematopoietin receptor family. Particular receptor subunits, the LIF receptor α-chain and gp130, which are components of several receptors (16) are also involved. IL-6, for example, binds with low affinity to its specific α-chain and with high affinity to this α-chain together with two gp130 subunits (18). Similarly, IL-11 binds to the interleukin-11 receptor α-chain (IL-11Rα) with low affinity and to a complex of IL-11Rα and gp130 with high affinity (19, 20).

The inventors have previously cloned cDNA encoding the IL-11Rα chain and in accordance with the present invention, the inventors have now created mice in which the low affinity IL-11 receptor (IL-11Rα) gene has been disrupted thereby ablating IL-11 signalling in the tissues of these mice. Surprisingly, the mice exhibited infertility. The present invention provides, therefore, a method for modulating fertility and pregnancy as well as a method for treating individuals with altered levels of IL-11, IL-11Rα or altered IL-11-receptor interaction.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention contemplates a method for modulating fertility in an animal, said method comprising administering to said animal an effective amount of IL-11 or a functional derivative or homologue thereof or an effective amount of an agonist or antagonist of interaction between IL-11 and IL-11Rα.

In a related aspect, the present invention provides a method for modulating fertility in an animal, said method comprising modulating the levels of expression of the gene encoding IL-11 and/or its receptor.

Another aspect of the present invention contemplates a method of enhancing fertility and/or maintenance of a pregnancy in a female animal, said method comprising administering to said female animal an effective amount of IL-11 or a functional derivative or homologue thereof or an agonist thereof for a time and under conditions sufficient for a pregnancy to proceed past the early post-implantation stage.

In a related aspect, the present invention relates to a method of enhancing fertility and/or maintenance of a pregnancy in a female animal, said method comprising modulating the levels of expression of the gene encoding IL-11 and/or its receptor for a time and under conditions sufficient for a pregnancy to proceed past the early post-implantation stage.

Yet another aspect of the present invention provides a method of enhancing fertility in a male animal said method comprising administering to said male animal, an effective amount of IL-11 or a functional derivative or homologue thereof or an agonist thereof.

In a related aspect, the present invention is directed to a method of enhancing fertility in a male animal said method comprising modulating the levels of expression of the gene encoding IL-11 and/or its receptor.

Still yet another aspect of the present invention provides a method of decreasing fertility or promoting termination of a pregnancy in a female animal, said method comprising administering to said female animal an effective amount of an antagonist of IL-11 or IL-11-receptor interaction.

In a related aspect, the present invention contemplates a method of decreasing fertility or promoting termination of a pregnancy in a female animal, said method comprising modulating the levels of expression of the gene encoding IL-11 and/or its receptor.

A further aspect of the present invention contemplates a method of decreasing fertility in a male animal, said method comprising administering to said male animal an effective amount of an antagonist of IL-11 or IL-11-receptor interaction.

In a related aspect, the present invention provides a method of decreasing fertility in a male animal, said method comprising modulating the levels of expression of the gene encoding IL-11 and/or its receptor.

Another aspect of the present invention contemplates an animal model comprising a mutation in at least one allele for IL-11 and/or IL-11Rα.

DETAILED DESCRIPTION OF THE PREFERRED EMBODIMENTS

Figure 1:
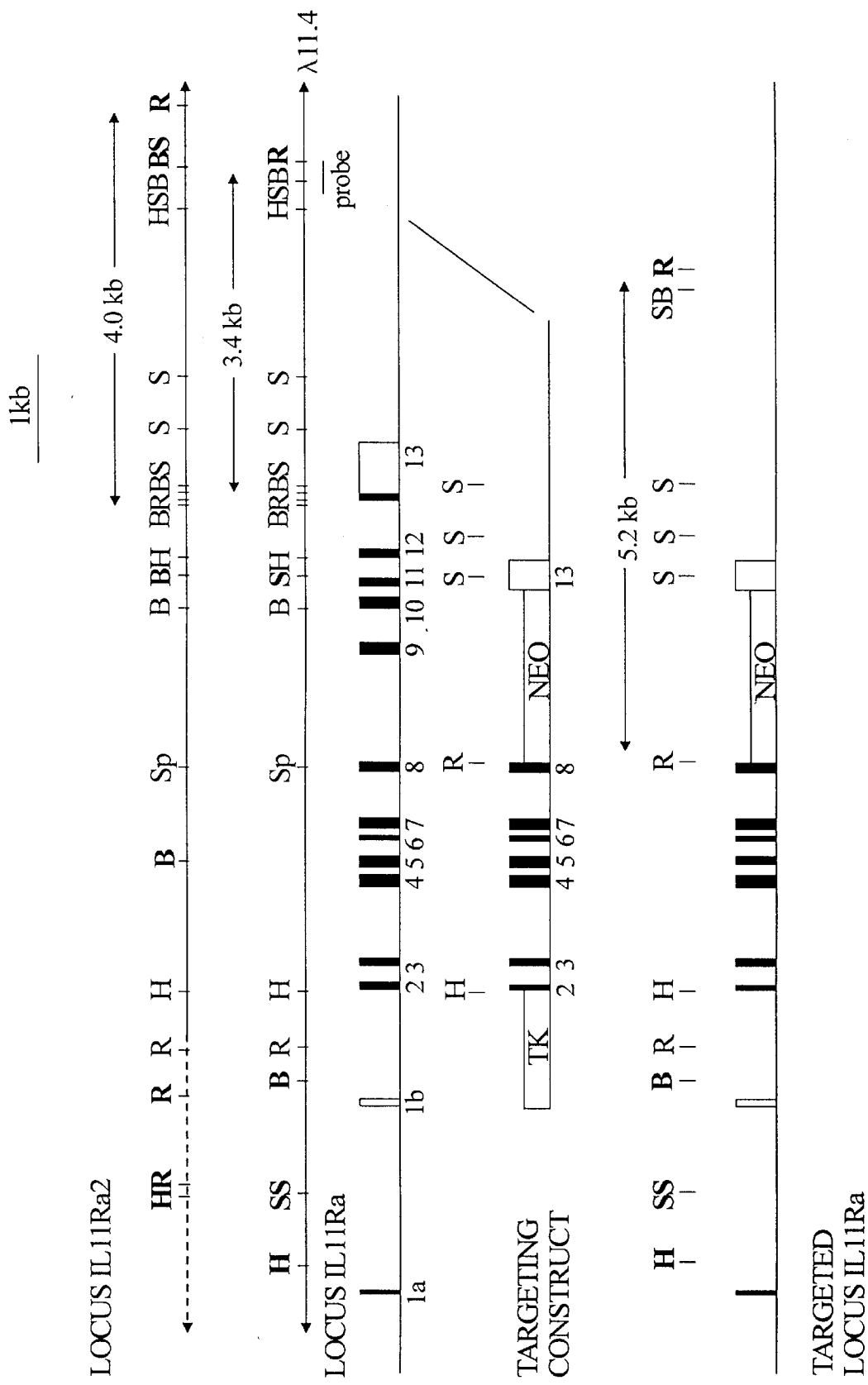
FIG. 1 is a diagrammatic representation showing disruption of the IL-11Rα locus by homologous recombination. Genomic organization of the murine IL-11Rα locus encoded by genomic phage clone λ11.4 is shown, the exons indicated as boxes and numbered, and coding regions shown in black. Dashed lines indicate parts of locus IL-11Rα2 that are not homologous with locus IL-11Rα. Restriction enzyme sites for locus IL-11Rα and IL-11Rα2 are indicated. Sites unique to a particular locus are shown in bold. EcoRI (R), BamHI (B), SacI (S), HindIII (H), and SphI (Sp). Shown below is the targeting vector containing the 5' and 3' homology regions and the cDNA encoding neomycin transferase (NEO) and thymidine kinase (TK) and the recombinant IL-11Rα locus. Location on the endogenous IL-11Rα locus of the probe used in Southern screening of embryonic stem cells and tail biopsies and the expected sizes of the endogenous IL-11Rα (3.4 kb), targeted IL-11Rα (5.2 kb) and endogenous IL-11Rα2 (4.0 kb) loci after EcoRI restriction digest are indicated.

One aspect of the present invention contemplates a method for modulating fertility in an animal, said method comprising administering to said animal an effective amount of IL-11 or a functional derivative or homologue thereof or an effective amount of an agonist or antagonist of interaction between IL-11 and IL-11Rα.

In a related aspect, the present invention provides a method for modulating fertility in an animal, said method comprising modulating the levels of expression of the gene encoding IL-11 and/or its receptor.

Reference herein to "animals" includes humans, primates, livestock animals (eg. horses, cattle, sheep, pigs, goats), companion animals (eg. dogs, cats), laboratory test animals (eg. mice, rats, guinea pigs) and captive wild animals (eg. deer, foxes, kangaroos).

The present invention is predicated in part on the surprising finding that IL-11, its receptor and/or the IL-11-receptor complex and/or other downstream signalling molecules are required for fertility and the maintenance of pregnancy. In female animals, normal IL-11 function is required for uterine decidual reaction which occurs post-implantation. Where a normal uterine decidual reaction does not occur, a pregnancy is aborted during the early post-implantation period, before the development of the chorioallantoic placenta. In male animals IL-11 function is required for normal spermatogenesis to occur.

The term "modulates" encompasses up-regulating or down-regulating fertility or the maintenance of a pregnancy. Accordingly, the present invention is applicable for facilitating fertility and pregnancy maintenance as well as fertility control and induction of abortion such as may be required in life threatening situations for a pregnant female. The ability to control fertility and pregnancy is also important for animal breeding such as in the horse industry and livestock animal industry. The present invention is applicable to modulating fertility in both female and male animals and, hence, is useful for birth control in females and males. The present invention is also applicable to fertility and pregnancy control in vermin animals such as but not limited to rodents, foxes, bats, rabbits, mice and rats.

Accordingly, another aspect of the present invention contemplates a method of enhancing fertility and/or maintenance of a pregnancy in a female animal, said method comprising administering to said female animal an effective amount of IL-11 or a functional derivative or homologue thereof or an agonist thereof for a time and under conditions sufficient for a pregnancy to proceed past the early post-implantation stage.

In a related aspect, the present invention relates to a method of enhancing fertility and/or maintenance of a pregnancy in a female animal, said method comprising modulating the levels of expression of the gene encoding IL-11 and/or its receptor for a time and under conditions sufficient for a pregnancy to proceed past the early post-implantation stage.

In a further related embodiment, the present invention provides a method of enhancing fertility in a male animal, said method comprising administering to said male animal, an effective amount of IL-11 or a functional derivative or homologue thereof or an agonist thereof.

In a related aspect, the present invention is directed to a method of enhancing fertility in a male animal, said method comprising modulating the levels of expression of the gene encoding IL-11 and/or its receptor.

IL-11 or its functional derivatives or homlogues may also be simultaneously or sequentially co-administered with one or more other cytokines such as but not limited to LIF, CNTF, IL-6 and/or OSM or their functional derivatives or homologues.

Another aspect of the present invention provides a method of decreasing fertility or promoting termination of a pregnancy in a female animal, said method comprising administering to said female animal an effective amount of an antagonist of IL-11 or IL-11-receptor interaction.

In a related aspect, the present invention contemplates a method of decreasing fertility or promoting termination of a pregnancy in a female animal, said method comprising modulating the levels of expression of the gene encoding IL-11 and/or its receptor.

A further aspect of the present invention contemplates a method of decreasing fertility in a male animal, said method comprising administering to said male animal an effective amount of an antagonist of IL-11 or IL-11-receptor interaction.

In a related aspect, the present invention provides a method of decreasing fertility in a male animal, said method comprising modulating the levels of expression of the gene encoding IL-11 and/or its receptor.

Where a female animal is pregnant, termination would normally occur early post-implantation, prior to development of the chorioallantoic placenta. Preferably, IL-11 or IL-11Rα expression or interaction is modulated to an extent to affect decidualization. For example, down-regulation of IL-11 or IL-11Rα or inhibiting interaction between IL-11 and IL-11Rα would facilitate defective decidualization.

The term "derivatives" as it applies to IL-11, its receptor and other cytokines and their receptors includes parts, fragments, portions, analogues and homologues. The derivatives may comprise single or multiple amino acid substitutions, deletions and/or additions. Agonists or antagonists may be derived from a target molecule (eg. IL-11 or its receptor) or may be a chemical molecule identified, for example, following natural product screening or screening of other chemical entities. Reference to "functional" molecules means that the molecules (eg. IL-11 or IL-11Rα) retain the ability to act in a manner for which they are normally associated. For example, a functional IL-11 or IL-11Rα would retain IL-11-mediated signalling function.

The term "analogues" includes, but is not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4amino-3-hydroxy-6-methylheptanoic acid, 2-thienyl alanine and/or D-isomers of amino acids. A list of unnatural amino acid, contemplated herein is shown in Table 1.

TABLE 1

| Nonconventional amino acid | Code |
| --- | --- |
| α-minobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |

TABLE 1-continued

| Nonconventional amino acid | Code |
| --- | --- |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenyl-ethylamino)cyclopropane | Nmbc |
| L-N-methylalanie | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalamine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylamine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylgiycine | Ncdec |
| N-cylcododecylglycine | Ncdod |

TABLE 1-continued

| Nonconventional amino acid | Code |
|---|---|
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of IL-11 capable of acting as antagonists or agonists of IL-11 or which can act as functional analogues of IL-11. Chemical analogues may not necessarily be derived from IL-11 but may share certain conformational similarities. Alternatively, chemical analogues may be specifically designed to mimic certain physiochemical properties of IL-11. Chemical analogues may be chemically synthesised or may be detected following, for example, natural product screening.

These types of modifications may be important to stabilise the analogues if administered to an animal.

Other derivatives contemplated by the present invention include a range of glycosylation variants from a completely unglycosylated molecule to a modified glycosylated molecule. Altered glycosylation patterns may result from expression of recombinant molecules in different host cells.

The cytokines such as IL-11, LIF, CNTF, IL-6 and OSM, their derivatives and homologues and their receptors (eg. IL-11Rα) are referred to herein as "therapeutic molecules".

The therapeutic molecules of the present invention are useful in a pharmaceutical composition together with one or more pharmaceutically acceptable carriers and/or diluents to modulate fertility and/or pregnancy. The term "active ingredient/s" is also used below to describe the therapeutic molecules.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 μg and 2000 mg of active compound.

The tablets, troches, pills, capsules and the like may also contain the components as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions, gels and foam. Topical application may be important during invasive procedures on female reproductive organs.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 μg to about 2000 mg. Expressed in proportions, the active compound is generally present in from about 0.5 μg to about 2000 mg/ml of carrier. In the case of compositions containing supplementary active ingredients, the dosages are determined by reference to the usual dose and manner of administration of the said ingredients.

The pharmaceutical composition may also comprise genetic molecules such as a vector capable of transfecting target cells where the vector carries a nucleic acid molecule capable of modulating IL-11 expression or IL-11 activity, or the expression or activity of the IL-11 receptor. The vector may, for example, be a viral vector. The present invention further contemplates gene therapy and other genetic means of modulating expression of the IL-11 gene or the IL-11 receptor gene. For example, co-suppression, anti-sense molecule and/or ribozyme molecules can be used to reduce expression of IL-11 or its receptor. Alternatively, more efficient promoters or other regulatory molecules may be employed to enhance expression.

The methods of the present invention may require the selective disruption of IL-11 or IL-11 mediated signalling such that the disruption affects only, or substantially only the reproductive system. This may be important where IL-11 is required for other physiologic activities such as modulating the immune system. Furthermore, the present invention may be applied to all loci encoding IL-11Rα. For example, some mice contain two loci for IL-11Rα: one of these, IL-11Rα is expressed only in testis, lymph node and thymus.

The present invention further contemplates an animal model comprising a mutation in at least one allele for IL-11 and/or IL-11Rα. Preferably the animal is a murine animal such as a mouse, the mutation may be a substitution, deletion and/or addition of one or more nucleotides in the IL-11 or IL-11Rα gene and includes deletion of the entire gene. In one embodiment, ES cells are isolated, the IL-11 or IL-11Rα gene disrupted or deleted by, for example, homologous recombination, antisense technology, riboenzymes or by co-suppression and the ES cells injected into blastocysts and implanted in a foster mother. The preferred offspring are IL-11−/− and/or IL-11Rα−/− but heterozygotes animals are also encompassed by the present invention.

The animal model of the present invention is useful for screening for therapeutic molecules capable of modulating fertility and pregnancy. For example, IL-11Rα−/− mice spontaneously abort at early post-implantation stage. Such mice may be subjected to a range of putative therapeutic molecules and then mice screened for successfully maintaining a pregnancy. Examples of putative therapeutic molecules include IL-11 or IL-11 complexed with its receptor. A similar protocol may be employed to screen for molecules capable of promoting fertility. The present invention further contemplates the treatment and/or prophylaxis of individuals with aberrations in IL-11 or IL-11 receptor. This might be particularly useful in treating female individuals.

The present invention is further described by the following non-limiting Examples.

The subject specification uses "IL-11Rα" and "IL-11Rα" interchangeably, with or without a hyphen to describe the IL-11 receptor locus in all animals.

The subject specification uses "IL-11Rα" and "IL11Rα" interchangedly (with or without a hyphen) to describe the IL-11 receptor locus in all animals.

EXAMPLE 1

Blue Dye Reaction

For blue dye reactions 100 μl of a 1% w/v solution of Chicago Sky Blue was injected into the tail vein on 4.5 or 5.5 d.p.c. Mice were killed 5 minutes later. Uteri were then fixed and serially sectioned to ascertain the number of implanting blastocysts.

EXAMPLE 2

Embryo Transfers

Superovulated females were mated and eight-cell to early morula-stage embryos were recovered from the oviduct at 2.5 d.p.c. Similar numbers of fertilised and unfertilised embryos were recovered from WT, IL11Rα−/− and IL11Rα−/− females. Healthy embryos were transferred to each uterine horn of 2.5 d.p.c. pseudopregnant recipient females. If recipients failed to litter at term, they were killed and the uterus was examined for evidence of resorption sites. All live-born pups were genotyped by Southern analysis of tail DNA (26).

EXAMPLE 3

Deciduomata

Mice 7–12 weeks of age were mated with vasectomized males. At 3.5 d.p.c., mice were anaesthetised and 25 µl of sesame oil (Sigma) was injected into one or both uterine horns. Mice were killed at 8.5 d.p.c. and each horn was weighed. In a further series of experiments, medroxyprogesterone acetate (Upjohn) in peanut oil was administered subcutaneously to control IL11Rα−/− mice as follows: 1 mg 1.5–2.5 d.p.c., 2 mg 3.5–7.5 d.p.c.

EXAMPLE 4

In situ Hybridisation

Tissues fixed in 4% v/v paraformaldehyde were dehydrated and embedded in paraffin. Adjacent 5 µm sections were processed and hybridised with ($\alpha^{33}$P)UTP labelled sense and antisense riboprobes as described (27). The placental lactogen-1 probe has been described (28). Two IL11Rα probes were used: 1155 bp HindIII and 436 bp SphI-SacI cDNA fragments subcloned into Bluescript (Stratagene). Both gave similar results. Two IL-11 probes were used: one as described (13) and a 460 bp fragment, generated by PCR, corresponding to nucleotides 48–508 of the murine IL-11 cDNA.

EXAMPLE 5

RNase Protection Analysis and Riboprobes

RNase protection analyses were performed using the RPAII Kit (Ambion). For IL-11, the assay was performed using 20 µg of total RNA. For other riboprobes, 10 µg of total RNA was used. For each riboprobe, the assays were repeated using two different sets of RNA samples prepared from timed matings of C57BL/6 mice. For samples collected prior to 4.5 d.p.c., the uteri were flushed to confirm the presence of fertilised embryos. The IL-11 and LIF riboprobes have been described previously (13, 29). The gp130 riboprobe was a 313 bp EcoRI-ApaI cDNA fragment cloned into Bluescript. The LIF receptor riboprobe was a 705 bp BglII-ApaI cDNA fragment cloned into Bluescript. This probe was able to detect the soluble form of the LIF receptor as a protected fragment of 411 bp (30). The actin riboprobe was purchased from Ambion.

EXAMPLE 6

Gene Targeting

Figure 2:
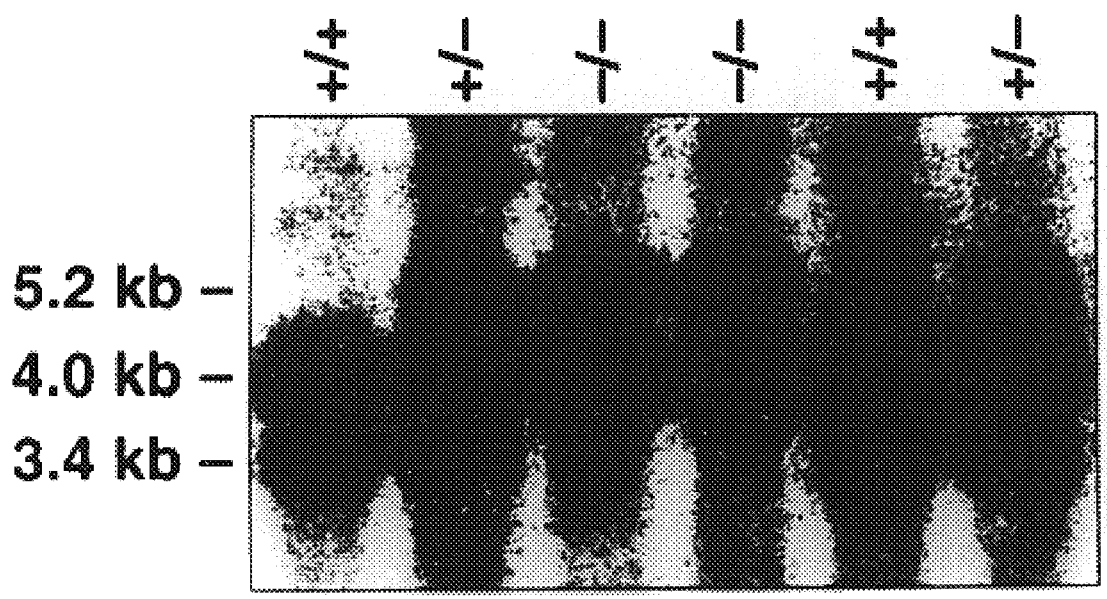
FIG. 2 is a photographic representation of a Southern analysis of EcoRI digested genomic DNA extracted from tails of mice derived from a cross between heterozygous (+/−) mice resulting in heterozygous, homozygous (−/−) and wild type (+/+) mice. Sizes of the endogenous IL-11Rα (3.4 kb) and the targeted IL-11Rα (5.2 kb) loci are indicated, as is the band for the endogenous IL-11Rα2 locus (4.0 kb).

The targeting construct was created using the pNTK vector. A 5' 2.6 kb HindIII-SphI fragment and a 3' 2.9 kb BamHI-HindIII fragment (both derived from genomic clone λ11.4, (21) were blunt-ended and inserted either side of the 1.8 kb pgkNEO cassette at the BamHI and ClaI sites. The NEO cassette replaced exons 9, 10, 11, 12, and exons 8 and 13 partially, resulting in a null mutation. The construct was linearised using XhoI and electroporated into W9.5 embryonic stem (ES) cells (22) which were selected using gancyclovir and G418 on day 2 and 10 respectively. Antibiotic resistant ES cell clones were isolated, amplified and screened by Southern blot by hybridizing Eco RI digested DNA to a 600 bp HindIII-EcoRI fragment derived from genomic clone λ11.4 (21) (FIG. 1). The probe (FIG. 1), which is situated in the IL-11Rα locus outside the targeting construct, allowed distinction between the endogenous loci (3.4 kb for locus IL-11Rα and 4.0 kb for locus IL-11Rα2) and mutant IL-11Rα loci (5.2 kb for locus IL-11Rα and 5.8 kb for locus IL-11Rα2). Genomic DNA was digested to completion with EcoRI, transferred to nylon membrane by capillary blotting and pre-hybridized and hybridized at 65° C. in a solution containing NaCl 1M, SDS 1% w/v, and dextran sulphate 10% w/v. The membranes were washed with a solution containing 0.2×SSC (1×SSC is 0.15 M NaCl, 0.015 M trisodium citrate) and 0.1% w/v SDS, at 65° C. and exposed to radiographic film for 18 h at −70° C. using intensifying screens. A single targeted clone for locus IL-11Rα was used to derive chimeric mice (23) which were mated with C57BL/6 female mice and the heterozygous offspring interbred to yield wild type (+/+), heterozygous (+/−), and mutant (−/−) mice. Mice genotypes were determined by Southern blot analysis of genomic DNA obtained from tail biopsies (FIG. 2).

EXAMPLE 7

Haematological Analysis

Orbital plexus blood was collected from anaesthetised mice and peripheral blood white cell count, haematocrit, and platelet counts were determined using either manual or automated (Sysmex K1000) counting techniques. Cell suspensions were made from bone marrow and spleen by standard techniques and total femoral and splenic cellularity was determined by haemocytometry after eosin staining. Manual 100–400 cell differential counts were performed on May-Grunwald Giemsa stained blood smears and cytocentrifuge preparations of bone marrow and spleen.

Bone marrow and spleen progenitors were assayed using semisolid agar and methyl cellulose cultures as previously described (23, 24). For each sample, $5 \times 10^4$ nucleated cells, were plated in triplicate in 1 ml cultures. Colony formation was stimulated by combinations of growth factors at the following final concentrations: murine granulocyte-macrophage colony stimulating factor (GM-CSF) 10 ng/ml, murine granulocyte-CSF 10 ng/ml, murine interleukin-3 (IL-3) 10, 1, 0.1 ng/ml, human IL-11 10 ng/ml, murine IL-6 500 ng/ml, recombinant human erythropoietin 4 U/ml murine stem cell factor (SCF) 10 ng/ml, human megakaryocyte growth and development factor. Colony numbers were enumerated after 7 days incubation in humidified atmosphere at 37° C. supplemented with 10% or 5% $CO_2$ (24). Cultures were fixed and stained using acetyl choline esterase, luxol fast blue and haematoxylin and the cellular composition of colonies determined.

EXAMPLE 8

Northern Analysis

Poly(A)$^+$ mRNA (3 µg/lane) was dissolved in 10 µl RNA loading buffer (2 mM 3-N-1morpholino) propane-sulfonic acid (MOPS), 1 mM EDTA, 5 mM sodium acetate pH 7.0, 50% v/v formamide, 6.3% v/v formaldehyde) and fractionated on 1% w/v agarose gel containing 0.22 M formaldehyde, 1×MOPS buffer (0.02 M MOPS, pH 7, 1 mM EDTA, 5 mM sodium acetate), 0.1 µg/ml ethidium bromide and run in 1×MOPS. RNA was transferred to nitrocellulose membrane (Hybond-C extra, Amersham) by capillary blotting with 20×SSC. Prehybridisation and hybridisation were carried out in a solution containing 50% v/v deionised formamide, 5×SSC, 0.1% w/v SDS, 300 μg/ml sheared herring sperm DNA and 2×Denhardtös (100×Denhardtös is 2% w/v Bovine Serum albumin, 2% w/v Ficoll and 2% w/v polyvinyl-pyrollidone). Washes were performed with 0.2× SSC, 0.1% w/v SDS at 65° C. Northern blots (FIG. 3) were first screened with a radiolabelled murine cDNA fragment, a 445 bp SphI/SacI restriction enzyme digest fragment, nucleotide 709–1158 from the murine IL-11Rα clone 30.1 (19), encoding the deleted exons 8–11. The filters were then stripped and reprobed with a radiolabelled 485 bp polymerase chain reaction (PCR) generated product encoding exons 2–6 and part of exon 7. PCR reactions were carried out in 50 μl volume containing 1×PCR buffer (Boehringer) 0.2 mM of each dNTP, 0.5 unit Taq Polymerase (Boehringer) and 200 ng of each primer: 5'-ATGAGCAGCAGCTGCTCAGGGCITG-3' (SEQ ID NO:1) and 5'-ACTTlCCCTCTGACTCTCAGCTCCTGG-3' (SEQ ID NO:2). Amplification conditions were: initial denaturation of 96° C. for 2 min followed by 25 cycles of 94° C. for 30 s, 55° C. for 30 s, 72° C. for 90 s. The PCR product was purified from an 2% w/v agarose gel using Qiaex Kit (Qiagen).

EXAMPLE 9

Generation of Mice with a Null Mutation of the IL-11Rα Gene

Figure 3A:
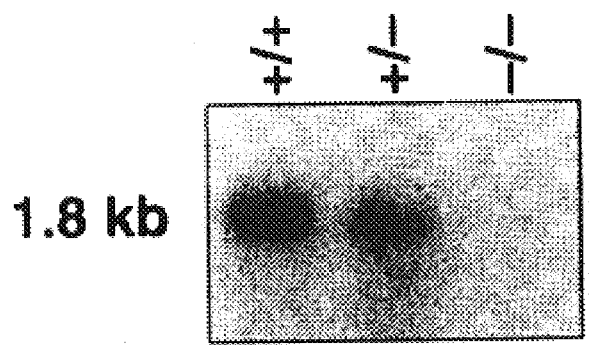
FIG. 3 is a photographic representation of a Northern analysis of poly(A)+ mRNA extracted from kidneys of heterozygous (+/−), homozygous (−/−) and wild type (+/+) mice. The blot was initially examined with a probe encoding the deleted region of the IL-11Rα locus (Panel A), then with a probe situated in the locus 5' of the deleted region (Panel B), and finally with a rat glyceraldehyde-3-phosphate dehydrogenase probe (GAPDH) to compare mRNA loading (Panel C). Also indicated is the size of the expected mRNA transcript (1.8 kb) in the heterozygous and wild type organs.
Figure 3B:
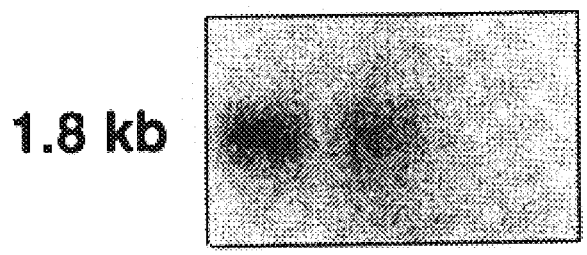
Figure 3C:
Figure 4A:
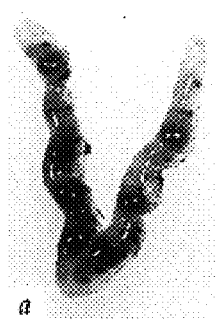
FIG. 4 is a photographic representation showing pregnant uteri of normal (left panels) and IL11Rα−/− mice (right panels) at 4.5–7.5 d.p.c. showing the reduced size of the decidual swellings in IL11Rα−/− mice. a,b, 4.5 d.p.c. c,d, 5.5 d.p.c. e,f, 6.5 d.p.c. g,h, 7.5 d.p.c. Mice were injected with Chicago Sky Blue dye 5 minutes prior to collecting the 4.5 and 5.5 d.p.c. specimens in order to visualise the implantation sites. The blue dye reaction is reduced in the IL11Rα−/− specimens.
Figure 4E:
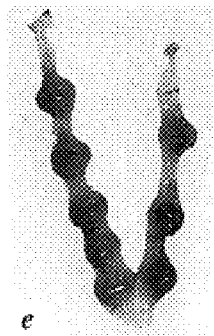
Figure 4B:
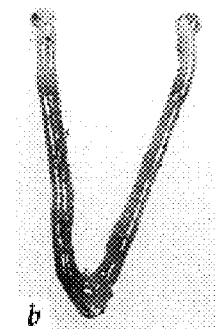
Figure 4F:
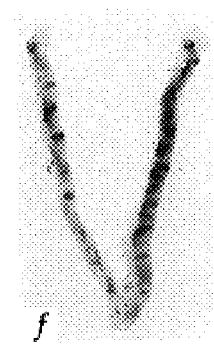
Figure 4C:
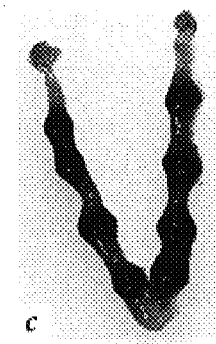
Figure 4G:
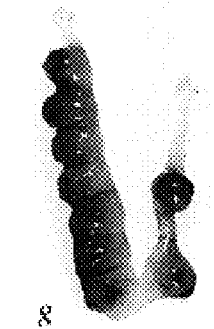
Figure 4D:
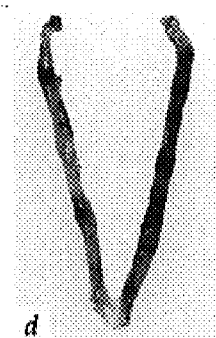
Figure 4H:
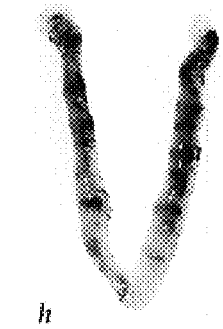

Mice heterozygous for the IL-11Rα (IL-11Rα+/−) mutation were interbred and the offspring genotyped (FIG. 2). Mice homozygous for the IL-11Rα mutation (IL-11Rα−/−) were born with Mendelian frequency (Table 2). To demonstrate that the mutation of the IL-11Rα gene in these mice resulted in a null mutation, expression of the gene was examined in several tissues by Northern analysis. Analysis of polyA+ RNA from IL-11Rα−/− kidney (a site which had previously been shown to express IL-11Rα at high level) using IL-11Rα cDNA probes lying both within the deleted region and 5' to it, did not reveal any IL-11Rα transcript (FIG. 3). Therefore the IL-11Rα−/− mice bear a null mutation of the IL-11Rα gene.

EXAMPLE 10

Haematopoiesis in the IL-11Rα−/− Mice

The IL-11Rα −/− mice appeared normal and thrived as well as their wild type litter mates. Gross anatomical examination and extensive histological examination did not reveal any abnormalities in IL-11Rα−/− mice of either sex. Peripheral blood counts, and differential counts of blood, spleen and bone marrow were unaltered. When bone marrow cells were cultured in semi-solid media with SCF, GM-CSF, IL-3 and IL-6 no differences were observed between the numbers or type of haematopoietic progenitor cells observed in the IL-11Rα−/− mice or in their wild-type littermates. IL-11 alone did not support colony formation in cultures from IL-11Rα−/− mice or controls. The synergy previously shown to occur with IL-11 and stem cell factor (SCF) (25) was observed in cultures of wild type bone marrow cells but was absent in cultures of IL-11Rα−/− bone marrow (Table 3). This provided further confirmation that the IL-11Rα disruption had resulted in a null mutation of the gene.

EXAMPLE 11

IL-11Rα−/− Female Mice are Infertile

As described above, mating IL-11Rα+/− mice resulted in the production of normal numbers of IL-11Rα−/− pups, demonstrating that the IL-11Rα−/− embryo was viable. However, matings between IL-11Rα−/− dams and wild type, IL-11Rα+/− or IL-11Rα−/− males never resulted in visible pregnancy or in the birth of pups (Table 4). Currently, female IL-11Rα −/− mice have been housed with proven stud males for periods of up to 100 days.

To investigate this further, the inventors mated two virgin female IL-11R+/− and two virgin female IL-11Rα−/− mice with wild type males and sacrificed them at 7.5 days post coitus (dpc) Whilst the uteri of the IL-11R+/− mice contained normal embryos within well-developed decidua, the uteri of the IL-11Rα−/− mice contained minute decidua, largely composed of the embryo-derived trophoblastic giant cells, with minimal decidual tissue and necrotic embryonic tissue.

The inventors also induced ovulation in the IL-11Rα mice and at 3.5 dpc and collected and examined the blastocysts. These blastocysts appeared normal.

These results indicate that in the IL-11Rα −/− female mice ovulation occurs normally, and the fertilised eggs develop into blastocysts and initiate implantation. The uterine decidual reaction which occurs post-implantation is abnormal in these mice and consequently the pregnancy is aborted during the early post-implantation period, well before the development of the chorioallantoic placenta.

EXAMPLE 12

Defective Uterine Decidualization in IL-11Rα−/− Mice

Virgin IL11Rα−/− females had normal estrus cycles, as indicated by the cytology of vaginal smears, and normal mating behaviour was observed when they were caged with males. The appearance and histology of the ovaries, oviducts, vagina and virgin uterus were normal. To elucidate the cause of the infertility, the inventors mated virgin C57BL/6 wild type (WT) and IL11Rα−/− females with males of both genotypes and examined the reproductive organs between 0.5 and 10.5 d.p.c. (day 0.5 being the day of detection of the vaginal plug). Preimplantation, the appearance, wet weight and the histology of the uteri from WT and IL11Rα−/− mice was similar and the number of fertilised and unfertilised ova or blastocysts recovered by flushing the oviduct at 0.5 d.p.c., or the uterus at 3.5 d.p.c., did not differ significantly. From 4.5–7.5 d.p.c., similar numbers of implantation sites were observed in both groups (WT: 5±4 per uterine horn, n=14, IL11Rα−/−: 5±3, n=25). The appearance and number of corpora lutea in the ovaries of IL11Rα−/− mice (9.2±0.6, n=6 mice, 6.5 d.p.c.) did not differ significantly from those present in WT mice (9.4±0.7, n=6 mice, 6.5 dp.c.). At 4.5 d.p.c. the size and intensity of the blue dye reaction surrounding implantation sites in the IL11Rα−/− uteri was reduced indicating reduced capillary permeability and blood flow in the uterine vascular bed at the site of blastocyst apposition (31) (FIGS. 4a–d). At 5.5–7.5 d.p.c. the decidua in the IL11Rα−/− uteri were considerably smaller than WT decidua and areas of haemorrhage were visible (FIGS. 4c–h).

Figure 5A:
FIG. 5 is a photographic representation showing decidual transformation of uteri of normal and IL11Rα−/− mice and 9.5 d.p.c. placental tissues. a,b, Sections of WT (a) and IL11Rα−/− (b) 4.5 d.p.c. uteri showing the reduced secondary decidual response to the implanting blastocyst in the IL11Rα−/− uterus. c,d, 5.5 d.p.c. WT (c) and IL11Rα−/− (d) uteri. e,f, Low power view of WT (e) and IL11Rα−/− (f) uteri at 6.5 d.p.c. The IL11Rα−/− uterus shows reduced decidual size, with hemorrhage in the uterine lumen. g, IL11Rα−/− uterus at 7.5 d.p.c., showing destruction of the abnormal decidua. h, High power view of a IL11Rα−/− decidua at 7.5 d.p.c., demonstrating disruption of the anti-mesometrial decidua and the absence of mesometrial decidualization. An intact 7.5 d.p.c. embryo is present. i, IL11Rα−/−7 d.p.c. deciduum, demonstrating the overgrowth of giant trophoblast cells in the mesometrial port of the deciduum. j, RNA in situ hybridisation was performed on a section of a 7.5 d.p.c. IL11Rα−/− decidua, using a probe for the giant-cell marker placental lactogen-1. Bright-field images of adjacent sections probed with left, sense, and right antisense probes. Counterstained with Mayers haematoxylin. k,l, 9.5 d p.c. WT (k) and IL11Rα−/− (l) placentas showing the absence of maternal decidual cells and the increased numbers of giant cells in the IL11Rα−/− uterus. 1: labrynthine trophoblast, s: spongiotrophoblast, g: giant cells, ma. maternal decidua. a–i, k, l, Haematoxylin and eosin stain. Scale bars: a, b, 20 $\mu$m, c,d, 40 $\mu$m, e–g, 200 $\mu$m, h,j, 50 $\mu$m.
Figure 5B:
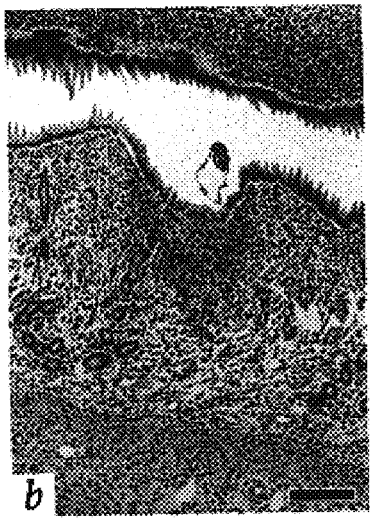
Figure 5C:
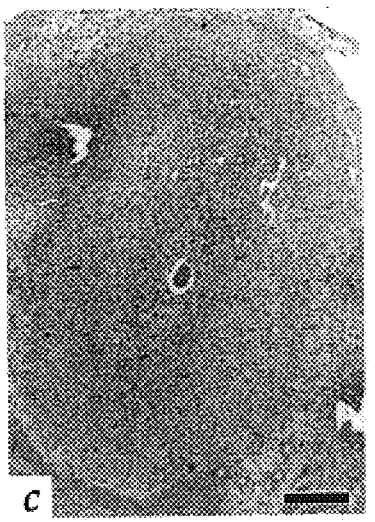
Figure 5D:
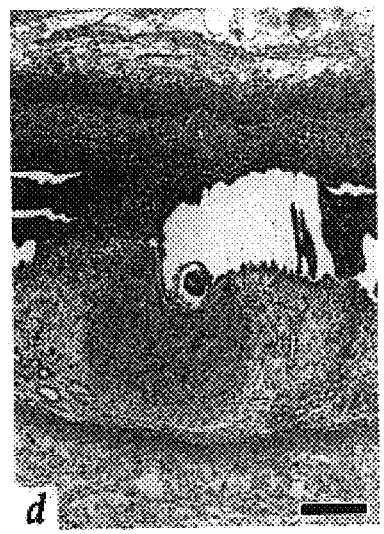
Figure 5E:
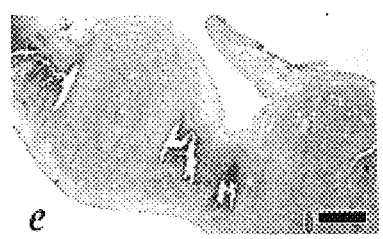
Figure 5G:
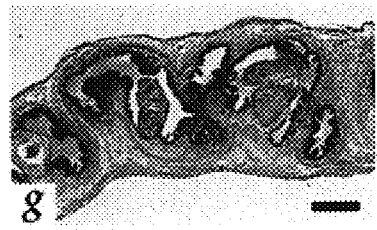
Figure 5F:
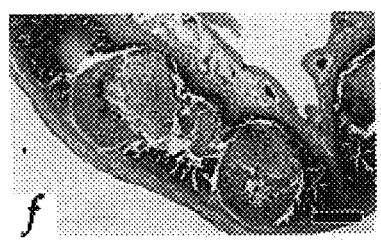
Figure 5H:
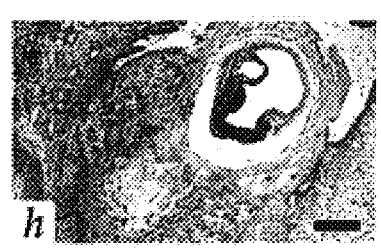
Figure 5I:

Microscopic examination of 4.5 d.p.c. decidua from IL11Rα−/− mice revealed that implantation had begun and an antimesometrial secondary decidual zone was apparent, but was markedly reduced in comparison with that seen in WT females (FIGS. 5a, b). By 5.5 d.p.c., in WT mice, the decidua had increased in size to completely surround the developing embryo (FIG. 5c). In the pregnant IL11Rα−/− mice, however, the secondary decidual zone remained markedly reduced (FIG. 5d). The cells of the secondary decidual zone were polyhedral and basophilic often with two or more nuclei and were morphologically indistinguishable from those seen in WF decidua. In sections of 6.5–7.5 d.p.c. uteri, the reduced size of the IL11Rα–/– decidua was striking (FIGS. 5e–g). The space normally occupied by the mesometrial decidua was invaded by very large cells resembling trophoblast giant cells (FIGS. 5h, i). The identity of these cells was confirmed by in situ hybridisation with probe for placental lactogen-1 (FIG. 5j), and proliferin the expression of which is restricted to trophoblast (28).

The number of secondary trophoblast giant cells present in the IL11Rα–/– decidua was markedly increased. The invasion of trophoblast cells was similar to that seen when ectoplacental cone tissue was grafted to ectopic sites such as the kidney, spleen, or non-pregnant uterus. Its occurrence in the IL11Rα–/– uteri suggests that signals from the mesometrial decidual tissues may normally regulate trophoblast development.

Figure 5K:
Figure 5J:
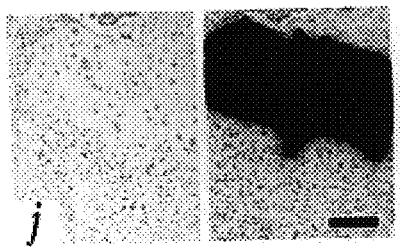
Figure 5L:

After 7.5 d.p.c., most embryos were necrotic and the uterine lumen was filled with blood and neutrophils. Increasing decidual disruption and infiltration by inflammatory cells was observed in sections of IL11Rα–/– uteri at 8.5 and 9.5 d.p.c. Live embryos were never observed after 10.5 d.p.c. Rarely (less than 1% of embryos examined) intact embryos were observed at 9 d.p.c. In most, the region normally occupied by the placenta was filled with fibrinoid material and inflammatory cells. In a few cases, however, the fetal components of the chorioallantoic placenta, including the chorionic plate, labyrinthine trophoblast and spongiotrophoblast were present. In these decidua, maternal venous sinuses were seen but the decidua basalis was entirely absent, being replaced by multiple layers of giant trophoblast cells, in contrast to the single-cell, discontinuous layer seen in normal 9.5 d.p.c. placentas (FIGS. 5k,l). This demonstrated that the fetal components of the murine placenta can form in the absence of the decidua basalis. The decidua capsularis was present in the decidua of the rare embryos surviving in 9 d.p.c. IL11Rα–/– uteri, although it was reduced in thickness in comparison with WT decidua. The abnormalities of decidualization seen in the IL11Rα–/– mice were similar whether the mutation was on a mixed (129Sv×C57BL/6) or inbred (129Sv) background and were unaffected by the genotype of the implanting embryo.

Successful implantation and post-implantation events in the uterus require synchrony between embryonic development and uterine receptivity. To exclude defects in embryonic development, 2.5 d.p.c. embryos were collected from WT, heterozygous and IL11Rα–/– females and were transfected to the uteri of recipient pseudopregnant female mice of all three genotypes. IL11Rα–/– embryos survived normally when placed in foster uteri, however WT embryos were unable to survive in the uteri of the IL11Rα–/– mice (Table 5), demonstrating that the homozygous material environment was deficient.

EXAMPLE 13

Figure 6:
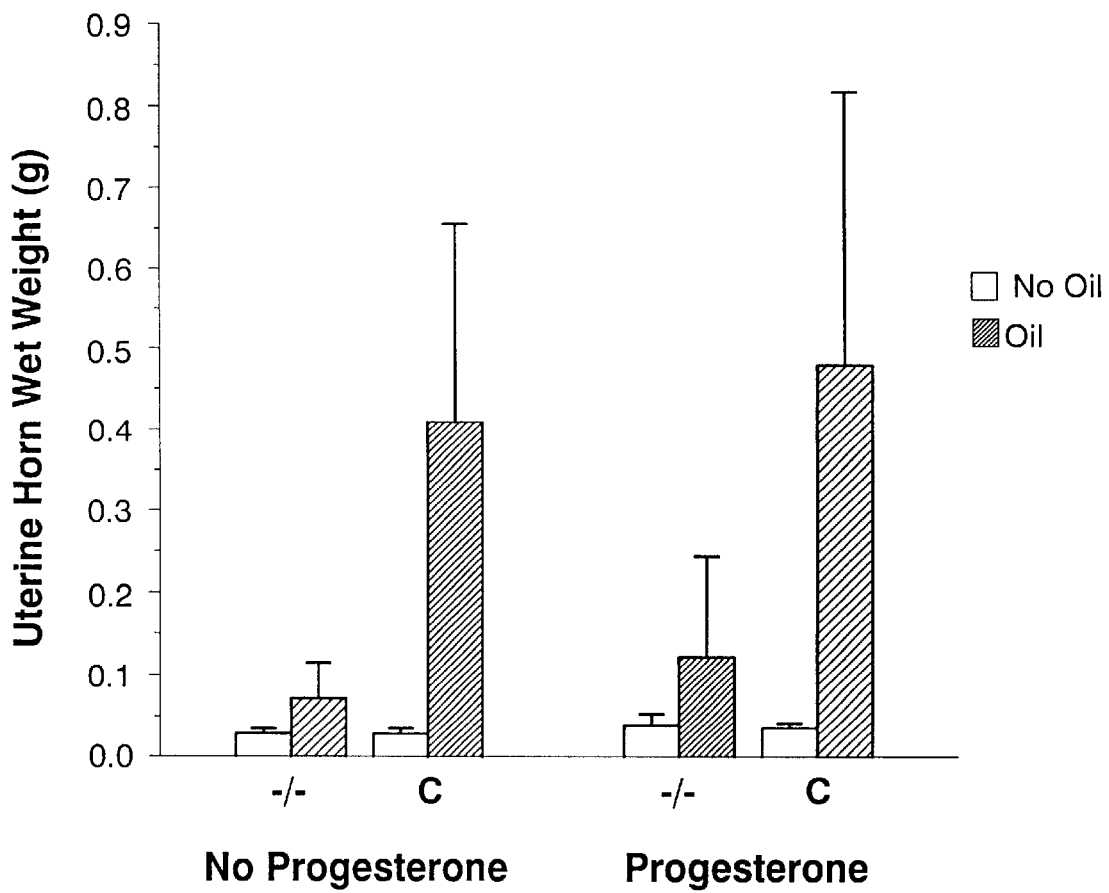
FIG. 6 is a graphical representation showing oil-induced deciduoma formation in pseudopregnant IL11Rα−/− and control uteri. Wet weight of single uterine horns from IL11Rα−/− (−/−) and control (IL11Rα−/−, C) mice. Mice were mated with pseudopregnant males and, at 3.5 d.p.c., were anaesthetised and one uterine horn was injected with 25 $\mu$l of sesame oil whilst the contralateral horn was used as a control. In some experiments progesterone was administered as described in the Examples. Results are shown as the mean and standard deviation of the weight of between 8 and 23 uterine horns. IL11Rα−/− oil-injected horns vs control oil-injected horns, with or without progesterone administration $p<0.001$ (Student's t-test).

Artificial Decidualization Is Impaired in IL11Rα–/– Mice and Is Not Rescued by Progesterone Administration The murine decidual reaction can be mimicked by the application of a stimulus, such as oil, to the lumen of the pseudopregnant uterus. The inventors compared deciduoma formation in response to an artificial stimulus in IL11Rα–/– uteri and control (IL11Rα–/–) mice. Pseudopregnancy was induced by mating with vasectomized males and at 3.5 d.p.c. sesame oil was introduced into one or both uterine horns anaesthesia. The mice were killed at 8.5 d.p.c. and the wet weight of the injected uterine horns was compared with that of uninjected controls. The decidual response was significantly greater in the control mice compared with IL11Rα–/– mice (FIG. 6). In several experiments, progesterone was administered to control and mutant mice. This did not rescue the decidualization defect observed in the IL11Rα–/– mice (FIG. 6). Histologically, the oil-induced deciduomata of control mice resembled decidua of a normal pregnancy. In comparison with control deciduomata, the overall size of the IL11Rα–/– deciduomata was reduced. However, in contrast to the IL11Rα–/– decidua induced by embryo implantation, in which mesometrial decidual tissue was absent, in a minority of oil-induced IL11Rα–/– deciduomata some mesometrial decidual tissue was observed.

EXAMPLE 14

Figure 7A:
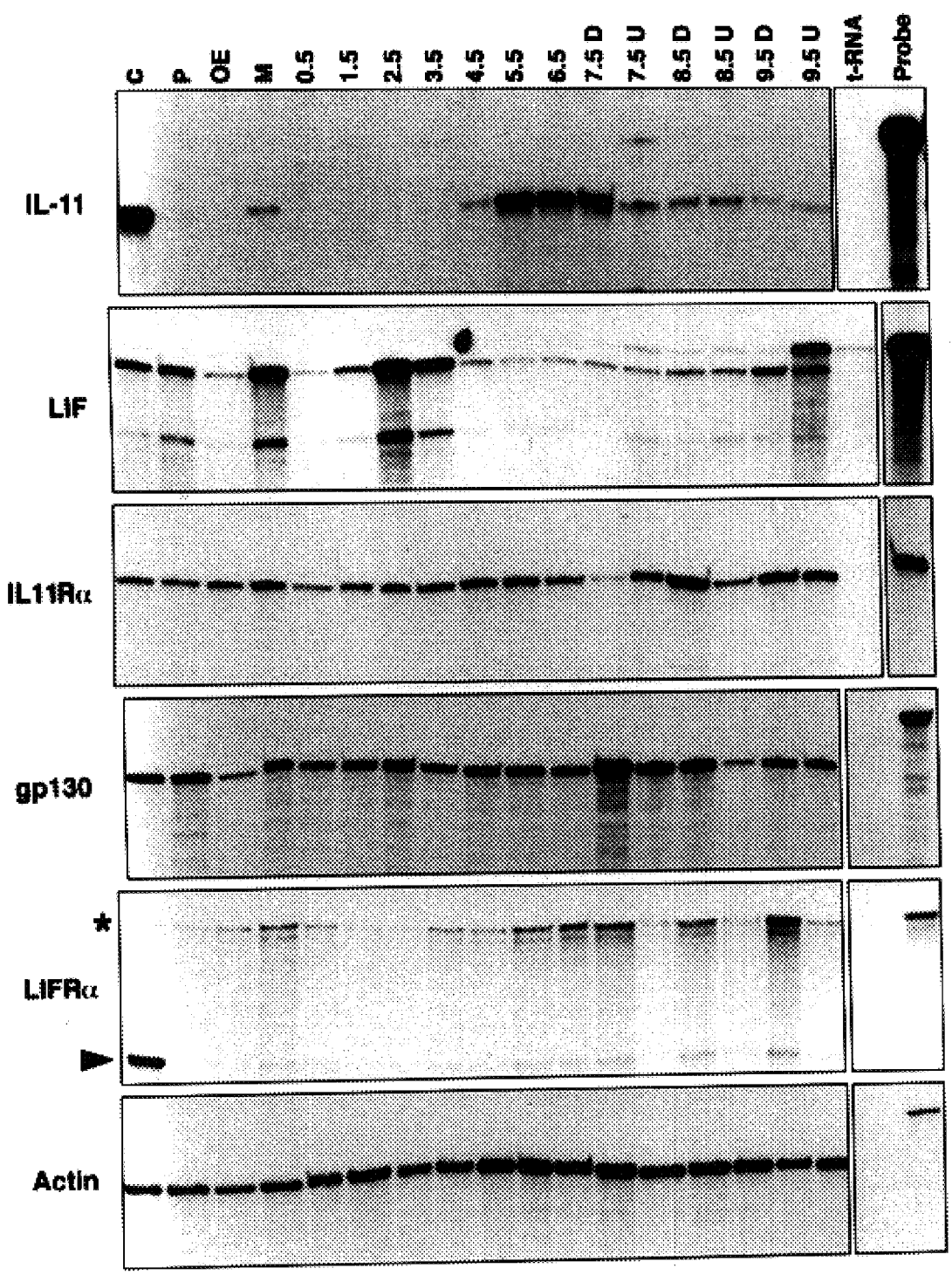
FIG. 7 is a photographic representation of gene expression in virgin and 0.5–9.5 d.p.c. uteri of C57BL/6 females and in oil-induced deciduomata (A) RNase protection analysis of gene expression in the uterus during the estrus cycle and from 0.5–9.5 d.p.c. 7.5–9.5 d.p.c. samples were divided into decidua+embryo (D) and uterus (U). Numbers refer to days post coitum. C: control, P: proestrus, OE: estrus, M: metestrus, Probe: full length probe, t-RNA: probe after RNase digestion. The lower band in the LIF panel is a partially degraded transcript. In the LIFRα panel the asterisk indicates the protected band corresponding to the full length transcript and the arrowhead indicates the protected band corresponding to the soluble form of the LIFRα. Control samples: IL-11: testis, LIF: STO cells, IL11Rα: kidney, gp130: liver, LIFRα: liver, Actin: testis. (B) RNase protection analysis of IL-11 gene expression in RNA prepared from deciduomata induced by injection of oil into pseudopregnant uteri of C57BL/6 mice. Numbers refer to days post coitum. Asterisk: undigested full length probe. Arrowhead: protected fragment.
Figure 7B:
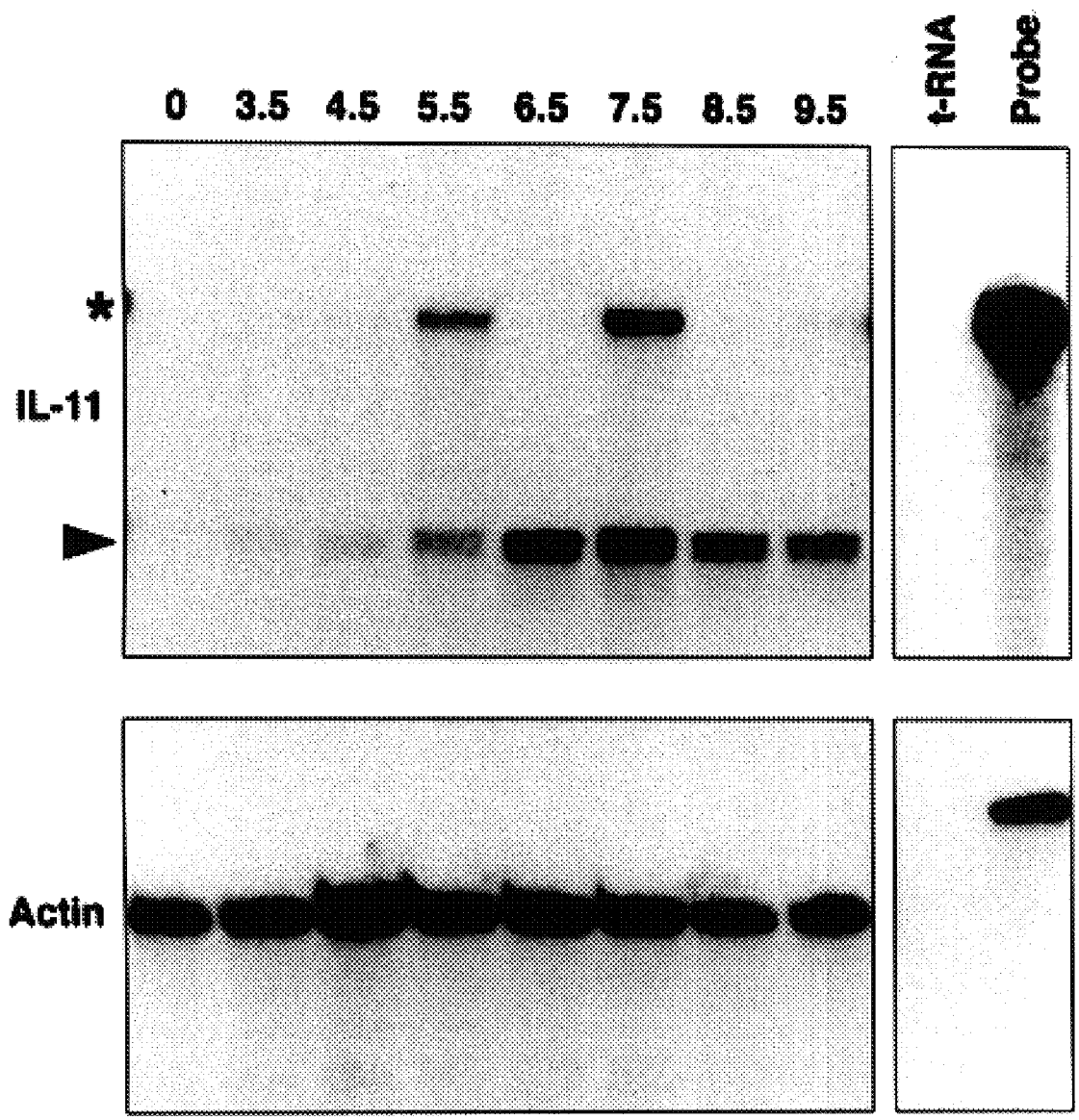

IL-11 and IL11Rα Are Normally Expressed in Pregnant Uterus During the Period of Decidualization Initially, the inventors examined the level of IL-11 mRNA in pre- and postimplantation uteri using RNase protection analysis. Expression of IL-11 was not detected in uteri in dioestrus, proestrus or estrus and was variably present at a low level during metoestrus. IL-11 mRNA was undetectable from 0.5–3.5 d.p.c., but was observed postimplantation, peaking at 5.5–7.5 d.p.c., after which it decreased (FIG. 7a). A similar time of onset of IL-11 expression was seen in oil-induced deciduornata (FIG. 7b). In contrast, LIF expression was maximal at 2.5–3.5 d.p.c. The expression of IL-11Rα, gp130 and the LIF receptor alpha chain did not alter significantly during pregnancy (FIG. 7a).

In situ hybridisation was used to determine the cell types expressing the genes encoding IL-11 and IL11Rα in the pregnant uterus. At 4.5 d.p.c. there was increased expression of IL-11 in the cells of the primary decidual zone. At 5.5, 6.5 and 7.5 d.p.c. IL-11 mRNA was detected throughout the decidua After 7.5 d.p.c., very little IL-11 mRNA was detectable in the decidua, consistent with the RNase protection analysis. Some IL11Rα expression was seen throughout the pregnant uterus at all timepoints examined. At 4.5 d.p.c., however, IL11Rα expression was augmented in the cells beginning to form the secondary decidual zone. By 6.5 d.p.c., IL11Rα expression was detected predominantly in the outer predecidual cells. By 8.5 d.p.c., expression of IL11Rα in the decidua had decreased. Positive signals were not detected in sections of IL11Rα–/– decidua hybridised with an antisense probe. Whilst the RNase protection analysis results showed that the overall level of IL11Rα expression in the uterus was constant during pregnancy, the in situ hybridisation results clearly indicated focally increased expression of IL11Rα in predecidual and decidual cells during the period of maximal transformation.

TABLE 2

Results of 40 intercrosses of IL-11Rα+/− mice

| | Genotype | |
|---|---|---|
| IL-11Rα+/+ | IL-11Rα+/− | IL-11Rα−/− |
| 82 | 185 | 100 |

TABLE 3

Culture of bone marrow from IL-11R−/− and wildtype littermates

| | Genotype | |
|---|---|---|
| Stimulus | +/+ | −/− |
| SCF | 80 ± 3 | 80 ± 16 |
| IL-11 | 1 ± 1 | 1 ± 1 |
| SCF + IL-11 | 110 ± 6 | 78 ± 11 |
| SCF(1;10) | 50 ± 7 | 53 ± 9 |
| SCF(1;10) + IL-11 | 95 ± 6 | 59 ± 14 |
| SCF(1;100) | 4 ± 3 | 3 ± 2 |
| SCF(1;100) + IL-11 | 9 ± 4 | 2 ± 1 |
| IL-3 | 92 ± 26 | 98 ± 17 |
| IL-3 + IL-11 | 125 ± 20 | 72 ± 25 |
| IL-3(1;10) | 55 ± 12 | 68 ± 16 |
| IL-3(1;10) + IL-11 | 111 ± 28 | 81 ± 25 |
| IL-3(1;100) | 15 ± 14 | 18 ± 7 |
| IL-3(1;100) + IL-11 | 46 ± 12 | 16 ± 4 |
| SCF + EPO | 27 ± 7 | 24 ± 10 |
| SCF + EPO + IL-11 | 42 ± 9 | 20 ± 11 |

50,000 nucleated bone marrow cells were cultured in triplicate plates with growth factors as indicated. Results are expressed as mean number of colonies±standard deviation of the results from three mice of each genotype.

TABLE 4

Average litter size from matings of IL-11Rα+/− and IL-11Rα−/− mice

| Mating pairs* | | |
|---|---|---|
| Female | Male | Average litter size |
| +/− | +/− | 9** |
| +/− | −/− | 9** |
| −/− | +/+ | 0 |
| −/− | +/− | 0 |
| −/− | −/− | 0 |

*n = 10
**average of 6 litters

TABLE 5

Transfer of IL11Rα−/− and WT 2.5 d.p.c. embryos

| Embryo donor Genotype* | no. | Recipient Genotype* | no. | no. pups born |
|---|---|---|---|---|
| WT | 24 | WT | 2 | 10 |
| IL11Rα+/− | 29 | WT | 3 | 18 |
| IL11Rα−/− | 48 | WT | 4 | 26 |
| WT | 60 | IL11Rα−/− | 5 | 0 |

*WT = C57BL/6
**WT = B6xCBA

BIBLIOGRAPHY

Du, X. X. and Williams, D. A. (1994). Interleukin-11: A multifunctional growth factor derived from the haemopoietic microenvironment. *Blood*, 83, 2023–2030.

Paul, S. R., Bennett, F., Calvetti J. A., Kelleher, K., Wood, C. R., O'Hara, R., Jr., Leary, A. C., Sibley, B., Clark, S. C., Williams, D. A. and Yang, Y.-C. (1990). Molecular cloning of a cDNA encoding interleukin 11, a stromal cell-derived lymphopoietic and hematopoietic cytokine. *Proc Natl Acad Sci U S A*, 87, 7512–6.

Kawashima, I., Ohsumi, J., Mita-Honjo, K., Shimoda-Takano, K., Ishikawa, H., Sakakibara, S., Miyadai, K. and Takiguchi, Y. (1991). Molecular cloning of a cDNA encoding adipogenesis inhibitory factor and identity with interleukin-11. *FEBS Lett*, 283, 199–203.

Du, x. x., Scott, d., Yang, Z. X., Cooper, R., Xiao, X. L. and Williams, D. (1995). Interleukin-11 stimulates multipotential progenitors, but not stem cells, in murine and human long-term marrow cultures. *Blood*, 86, 128–134.

Quesniaux, V. F. J., Clark, S. C., Turner, K. and Fagg, B. (1992). Interleukin-11 stimulated multiple phases of erythropoiesis in vitro. *Blood*, 80, 1218–1223.

Bruno, E., Briddell, R. A., Cooper, R. J. and Hoffman, R. (1991). Effects of recombinant interleukin 11 on human megakaryocyte progenitor cells. *Exp Hematol*, 19, 378–381.

Yin, T. G., Schendel, P. and Yang, Y. C. (1992). Enhancement of in vitro and in vivo antigen-specific antibody responses by interleukin-11. *J Exp Med*, 175, 211–216.

Baumann, H. and Schendel, P. (1991). Interleukin-11 regulates the hepatic expression of the same plasma protein genes as interleukin-6. *J Biol Chem*, 266, 20424–20427.

Mehler, M. F., Rozental, R., Dougherty, M., Spray, D. and Kessler, J. A. (1993). Cytokine regulation of neuronal differentiation of hippocampal progenitor cells. *Nature*, 362, 62–65.

Girasole, G., Passeri, G., Jilka, R. L. and Manolagas, S. C. (1994). Interleukin 11: a new cytokine critical for osteoclast development. *J Clin Invest*, 93, 1516–1424.

Du, X. X., Neben, T., Goldman, S. and Williars, D. A. (1993). Effects of recombinant human interleukin-11 on hematopoietic reconstitution in transplant mice: acceleration of recovery of peripheral blood neutrophils and platelets. *Blood*, 81, 27–34.

Du, X. X., Doerschuk, C. M., Orazi, A. and Williams, D. A. (1994). Bone marrow stromalderived growth factor, interleukin-11, stimulates recovery of small intestinal mucosal cells after cytoablative therapy. *Blood*, 86, 33–37.

Du, X. X., Everett, E. T., Wang, G., Lee, W.-H., Yang, Z. and Williams, D. A. (1996). Murine interleukin-11 (IL-11) is expressed at high levels in the hippocampus and expression is developmentally regulated in the testis. *J Cell Physiol*, 168, 362–372.

Rose, T. M. and Bruce, A. G. (1991). Oncostatin M is a member of a cytokine family that includes leukemia-inhibitory factor, granulocyte colony-stimulating factor, and interleukin 6. *Proc Natl Acad Sci U S A*, 88, 8641–5.

Hilton, D. J. (1992). LIF: lots of interesting functions. *Trends Biochem Sci*, 17, 72–6.

Kishimoto, T., Akira, S., Narazaki, M. and Taga, T. (1995). Interleukin-6 family of cytokines and gp130. *Blood*, 86, 1243–1254.

Davis, S. and Yancopoulos, G. D. (1993). The molecular biology of the CNTF receptor. *Curr Opin Cell Biol*, 5, 281–5.

Murakari, M., Hibi, M., Nakagawa, N., Nakagawa, T., Yasukawa, K., Yamanishi, K., Taga, T. and Kishimoto, T. (1993). IL-6-induced homodimerization of gp130 and associated activation of a tyrosine kinase. *Science,* 260, 1808–10.

Hilton, D. J., Hilton, A. A., Raicevic, A., Rakar, S., Harrison-Smith, M., Gough, N. M., Bebley, C. G., Metcalf, D., Nicola, N. A. and Willson, T. A. (1994). Cloning of a murine IL-11 receptor α-chain; requirement for gp130 for high affinity binding and signal transduction. *EMBO J,* 13,4765–4775.

Nandurkar, H. H., Hilton, D. J., Nathan, P., Willson, T. and Begley, C. G. (1996). The human IL-11 receptor requires gp130 for signalling: demonstration by molecular cloning of the receptor. *Oncogene,* 12, 585–593.

Robb, L., Hilton, D. J., Willson, T. A. and Begley, C. G. (1996). Structural analysis of the gene encoding the murine interleukin-11 receptor α-chain and a related locus. *J Biol Chem,* 271, 13754–13761.

Carney, E. W., Prideaux, V., Lye, S. J. & Rossant, J. (1993) Progessive expression of trophoblast-specific genes during formation of mouse trophoblast giant cells in vitro. *Mol. Reprod. Dev.,* 34, 357–368.

Bhatt, H., Brunet, L. J. & Stewart, C. L. (1991) Uterine expression of leukaemia inhibitory factor coincides with the onset of blastocyst implantation. *Proc. Nat. Acad. Sci. USA* 88, 11408–11412.

Tomida, M., Yamamoto-Yamaguchi, Y & Hozumi, M. (1994) Three different cDNAs encoding mouse D-Factor/LIF receptor. *J. Biochem*115, 557–562.

Psychoyos, A. (1973) *Handbook of Physiology* (eds. Greep, R. O., Astwood, E. G. & Geiger, S. R.) 187–215 (American Physiological Society, Washington D.C., 1973).

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
atgagcagca gctgctcagg gctg                                    24

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 2
actttccctc tgactctcag ctcctgg                                 27

Szabo, P. and Mann, J. R. (1994). Expression and methylation of imprinted genes during in vitro differentiation of mouse parthenogenetic and androgenetic embryonic stem cell lines. *Development,* 120, 1651–1660.

Robb, L, Lyons, I., Li, R., Hartley, L., Harvey, R. P., Kontgen, F. and Begley, C. G. (1995). Absence of yolk sac hematopoiesis from mice with a targeted disruption of the sci gene. *Proc Natl Acad Sci USA,* 92, 7075–7079.

Metcalf, D. (1984). Clonal Culture of Hemopoietic cells: techniques and applications. (Elsevier: Amsterdam, The Netherlands)

Tsuji, K., Lyman, S. D., Sudo, T., Clark, S. C. and Ogawa, M. (1992). Enhancement of murine hematopoiesis by synergistic interactions between steel factor (ligand for c-kit), interleukin-11, and other early acting factors in culture. *Blood,* 79, 2855–60.

Nandurkar, H. H., et al (1997) Adult mice with a targeted mutation of the IL-11 receptor (IL11Rα) display normal hematopoiesis. *Blood,* 90, 2148–2159.

Lyons, I et al (1995) Myogenic and morphogenetic defects in the heart tubes of murine embryos lacking the homeobox geen Nkx2-5. *Genes Dev,* 9, 1654–1666.

What is claimed is:

1. A method for enhancing fertility in a female animal, said method comprising administering IL-11 to said animal to agonise the interaction between IL-11 and IL-11Rα, and thereby enhancing decidualization.

2. A method of down-modulating fertility in a female animal, said method comprising administering IL-11Rα, to antagonize the interaction between IL-11 and IL-11Rα, and to induce or facilitate defective decidualization.

3. The method of claim 1 or 2 wherein the animal is a human, primate, livestock animal, companion animal, laboratory test animal or a captive wild animal.

4. The method of claim 1 wherein the IL-11 is co-administered with one or more cytokines.

5. The method of claim 4 wherein the co-administered cytokine is selected from LIF, CNTF, IL-6 and OSM or homologues thereof.

* * * * *